United States Patent [19]

Schmidt et al.

[11] Patent Number: 5,624,487

[45] Date of Patent: Apr. 29, 1997

[54] PREPARATION OF BLUISH LUSTER PIGMENTS

[75] Inventors: Helmut Schmidt; Werner Ostertag, both of Osthofen; Hermann Bidlingmaier, Offenburg; Norbert Mronga, Dossenheim; Juan A. G. Gomez, Ludwigshafen; Claus Kaliba, Neuhofen; Raimund Schmid, Neustadt; Raymond Ellinghoven, Marbach, all of Germany

[73] Assignee: BASF Aktiengesellschaft, Ludwigshafen, Germany

[21] Appl. No.: 622,593

[22] Filed: Mar. 26, 1996

[30] Foreign Application Priority Data

Mar. 30, 1995 [DE] Germany ............... 195 11 697.6

[51] Int. Cl.$^6$ ............... C09C 1/00; C04B 14/20
[52] U.S. Cl. ............... 106/417; 106/415; 106/436; 428/363; 428/404; 428/406
[58] Field of Search ............... 106/408, 415, 106/417, 436; 428/195, 209, 363, 403, 404, 406

[56] References Cited

U.S. PATENT DOCUMENTS

| 4,623,396 | 11/1986 | Kimura et al. ............... 106/417 |
| 4,948,631 | 8/1990 | Ostertag et al. ............... 106/417 |
| 4,978,394 | 12/1990 | Ostertag et al. ............... 106/415 |

FOREIGN PATENT DOCUMENTS

| 0332071A1 | 9/1989 | European Pat. Off. . |
| 0525526A1 | 2/1993 | European Pat. Off. . |
| 3433657A1 | 3/1985 | Germany . |
| 59-126468-A | 7/1984 | Japan . |
| 61-192749-A | 2/1985 | Japan . |
| 60-184570-A | 9/1985 | Japan . |
| 164-653-A | 1/1986 | Japan . |

OTHER PUBLICATIONS

Patent Abstracts of Japan, vol. 9, No. 78 (C–274), Apr. 6, 1985, JP–A–59 212422, Dec. 1, 1984.

*Primary Examiner*—Mark L. Bell
*Assistant Examiner*—Michael Marcheschi
*Attorney, Agent, or Firm*—Oblon, Spivak, McClelland, Maier & Neustadt, P.C.

[57] ABSTRACT

Preparation of bluish luster pigments by treating titania-coated silicatic platelets with a reducing gas mixture, which comprises treating titania-coated silicatic platelets whose titania coating has a geometric layer thickness of from 10 to 60 nm at from 800° to 900° C. with a gas mixture comprising a vaporized organic compound and ammonia, and also bluish luster pigments based on silicatic platelets comprising a reduced titania coating with a geometric layer thickness of from 10 to 60 nm and CIELAB color coordinates $-2 \leq a^* \leq 2$ and $b^* \leq -20$ (measuring angle 20°, standard illuminant D65).

11 Claims, No Drawings

PREPARATION OF BLUISH LUSTER PIGMENTS

The present invention relates to a novel process for preparing bluish luster pigments by treating titania-coated silicatic platelets with a reducing gas mixture.

The invention also relates to novel bluish luster pigments based on silicatic platelets comprising a reduced titania coating with a geometric layer thickness of from 10 to 60 nm and CIELAB color coordinates $-2 \leq a^* \leq 2$ and $b^* \leq -20$ (measuring angle 20°, standard illuminant D65) and to the use thereof for coloring paints, inks, including printing inks, plastics, glasses, ceramic products and decorative cosmetic preparations.

Reduced titania-coated luster pigments whose $TiO_2$ coating comprises or has been wholly converted to reduced titanium species (oxidation state of the titanium: from <4 to 2) have long been known as "dark pearl luster pigments" for the blue to black hue range, and are notable for good hiding power, color strength and luster.

It is known to prepare said dark pearl luster pigments by treating titania-coated mica pigments with reducing gases at temperatures from 600° to 900° C.

The reducing gases used have been propane, whose use gives rise not only to reduced titanium species but also to carbonaceous products (JP-A-192 749/1985, EP-A-525 526), hydrogen (JP-A-192 749/1985), and predominantly ammonia and ammonia/nitrogen mixtures. The products obtained are described as blue, bluish black or black and the reduced species as lower titanium oxides such as $Ti_3O_5$, $Ti_2O_3$ to TiO, titanium oxynitrides and also titanium nitride (JP-A-164 653/1983, JP-A-126 468/1984, JP-A-184 570/1985 and DE-A-34 33 657).

EP-A-332 071 finally also discloses a process for preparing particularly bluish pearl luster pigments wherein silvery or blue-reflecting $TiO_2$-coated micas (optical $TiO_2$ layer thickness from 50 to 100 nm or from 300 to 340 nm) are reduced with ammonia at from 750° to 850° C. while under constant agitation.

Very particularly bluish and also clean-hued pigments, however, are obtained only by reducing the costly, blue-reflecting micas having a high $TiO_2$ layer thickness, while treatment of the less costly silvery micas having a low $TiO_2$ layer thickness produces, even after long treatment times, blues which, although intensive ($b^* \approx -20$), have a high green content ($a^* \approx -5$).

It is an object of the present invention to make possible the preparation of particularly bluish, clean-hued pearl luster pigments in an inexpensive, reproducible manner.

We have found that this object is achieved by a process for producing bluish luster pigments by treating titania-coated silicatic platelets with a reducing gas mixture, which comprises treating silicate platelets having a titania coating of a geometric layer thickness of 10 nm to 60 nm with a reducing gas mixture of a vaporized organic compound and ammonia at a temperature of 800°–900° C.

The invention further provides the above-defined bluish luster pigments and their use for coloring paints, inks, including printing inks, plastics, glasses, ceramic products and decorative cosmetic preparations.

Suitable platelet-shaped silicatic substrate materials for the bluish luster pigments of the present invention include in particular light-colored or white micas, particularly preferably flakes of preferably wet-ground muscovite. It is of course also possible to use other natural micas, such as phlogopite or biotite, artificial micas, talc and glass flakes.

The substrate particles are coated with a layer which consists essentially of titanium dioxide and may contain minor proportions (generally <5% by weight) of further, preferably colorless, metal oxides such as zirconium dioxide, tin dioxide, aluminum oxide and silicon dioxide, and have a geometric layer thickness of from typically 10 to 60 nm, preferably from 20 to 40 nm.

These silvery pearl luster pigments are generally known (cf. for example DE-A-14 67 468, DE-A-32 37 264 or DE-A-20 09 566) and commercially available under the names IRIODIN® (E. Merck, Darmstadt), FLONAX® (Kemira Oy, Pori, Finland) or MEARLIN® (Mearl Corporation, Ossining, N.Y.).

It will be appreciated that the process of the present invention could also start from pearl luster pigments having a blue interference color, but the silvery pigments are preferable for reasons of cost.

The size of the substrate particles is not critical per se and can be adapted to the particular application. Typically, the platelet-shaped particles have average largest diameters of from about 1 to 200 µm, in particular from about 5 to 100 µm, and thicknesses of from about 0.1 to 1 µm, in particular about 0.5 µm. Their specific free surface area (BET) is customarily within the range from 1 to 15 $m^2/g$, in particular from 3 to 12 $m^2/g$.

In the novel process for preparing bluish luster pigments, the silvery titania-coated silicatic platelets are generally treated at from 800° to 900° C., preferably at from 820° to 880° C., with a gas mixture comprising a vaporized organic compound and ammonia.

Suitable organic compounds include not only gaseous compounds but also compounds which are liquid or even solid at room temperature and can be vaporized.

Preference is given to hydrocarbons, especially saturated aliphatic $C_1$–$C_8$-hydrocarbons such as pentane, isopentane, neopentane, hexane, heptane and octane and also branched isomers thereof and very particularly methane, ethane, propane and butane and isomers thereof, also unsaturated aliphatic $C_2$–$C_4$-hydrocarbons such as ethene, propene, butene and isomers thereof and aromatic hydrocarbons such as benzene and toluene.

It is of course also possible to use mixtures of these hydrocarbons, as present in natural gas, for example.

It is also possible to use organic compounds which contain not only carbon and hydrogen but also oxygen and/or nitrogen, in which case, however, not more than one oxygen and/or nitrogen atom should be present in the molecule per carbon atom.

Examples of suitable compounds of this kind include $C_1$–$C_5$-alcohols such as methanol, ethanol, propanol and isopropanol, $C_3$–$C_7$-ketones such as acetone, di-$C_1$–$C_2$-alkyl ethers such as dimethyl and diethyl ether and cyclic ethers such as tetrahydrofuran and also mono-$C_1$–$C_5$-alkylamines and monoarylamines such as methylamine, ethylamine, propylamine and aniline, which can also be used alone, without ammonia, if the carbon/nitrogen ratio conforms to the composition desired for the reducing gas mixture. Generally, however, amines are more difficult to handle.

The volume ratio of the preferred components in the reducing gas mixture, ammonia and hydrocarbon, can be widely varied and is generally within the range from 99:1 to 50:50; especially if methane, ethane and/or propane are used, a volume ratio of from 95:5 to 70:30 is preferred.

Advantageously the reducing gas mixture is diluted with an inert gas such as nitrogen. This is advisable in particular when the organic compound has first to be evaporated and is ideally carried into the reaction space by the inert gas stream. A particular advantage is a nitrogen content of from 10 to 60% by volume, based on the total amount of gas.

However, it is also possible to use a gas mixture consisting of hydrocarbon and ammonia only.

The action of the gas mixtures comprising organic compound (especially hydrocarbon) and ammonia reduces the $TiO_2$ layer of the pigment (at least) in part in the case of the present invention too to form the reduced species described at the beginning. The degree of reduction increases with increasing reaction temperature and increasing reaction time; also on the increase, in parallel, is the nitrogen content of the luster pigments, i.e. the proportion of nitridic titanium compounds.

Generally, the luster pigments obtained have nitrogen contents of from 0.2 to 3% by weight, preferably from 0.2 to 2% by weight.

It has been found that the process of the present invention, i.e. reduction with hydrocarbon-ammonia mixtures, surprisingly introduces only very small amounts of carbon into the luster pigments (or into their reduced titanium dioxide coating), generally only from 1 to 20% by weight of the amount of carbon introduced under the same conditions and the use of hydrocarbon alone.

The products are therefore particularly bluish and also clean-hued luster pigments which generally have CIELAB coordinates $-2 \leq a^* \leq 2$ and $b^* \leq -20$ (measuring angle 20°, standard illuminant D65).

The reduction according to the present invention generally takes from 1 to 4 h, in particular from 2 to 3 h, and hence is distinctly faster than if ammonia is used alone.

The process of the present invention can be carried out not only continuously, for example in a heated, inertized rotary tube oven fed with the mica pigment and with a mixture of the reducing gases with an inert gas, but also batchwise, for example in a heated, inertized rotary drum with gas inlet and outlet or a heated, inertized fluidized bed reactor, and the mica platelets advantageously come into contact with the reducing gas on all sides, which, in the rotary tube oven or in the rotary drum, is preferably achieved by means of trip strips.

After the reduction has ended, the luster pigment is preferably cooled down under an inert gas. If desired, a deagglomerating step can follow, for example in a mixer equipped with beater blades.

The process of the present invention makes it possible to prepare particularly bluish (and clean-hued) luster pigments reproducibly in an economical manner (inexpensive starting materials, short treatment times).

The luster pigments of the present invention are advantageously useful for many purposes, such as the coloring of plastics, glasses, ceramic products, decorative cosmetic preparations and in particular paints and inks, including printing inks. All industrially customary printing processes can be used, for example screen printing, intaglio printing, bronze printing, flexographic printing and offset printing.

For these purposes, the luster pigments of the present invention can also be used with advantage in a blend with transparent and hiding white, colored and black pigments and also conventional luster pigments.

Examples of suitable luster pigments include singly or multiply metal oxide-coated mica and metal pigments, uncoated metal pigments based on aluminum, black luster pigments, such as platelet-shaped graphite and magnetite pigments, and platelet-shaped metal oxide pigments, for example based on iron(III) oxide and bismuth oxychloride.

Suitable inorganic pigments include for example titanium oxides, doped titanium oxides such as nickel titanium yellow, iron oxides, bismuth vanadates, colored spinels, chromate and cadmium pigments.

Suitable organic pigments include for example monoazo pigments (e.g. products derived from acetoacetarylide derivatives or from β-naphthol derivatives), laked monoazo dyes such as laked β-hydroxynaphthoic acid dyes, disazo pigments, condensed disazo pigments, isoindoline derivatives, derivatives of naphthalene-dicarboxylic acid, derivatives of perylenetetracarboxylic acid, anthraquinone pigments, thioindigo derivatives, azomethine derivatives, quinacridones, dioxazines, pyrazoloquinazolones, indanthrone and phthalocyanine pigments.

EXAMPLES

Preparation and evaluation of luster pigments according to the present invention The luster pigments are prepared in a mechanically rotatable single-neck quartz round-bottom flask equipped with a gas inlet and outlet in the axis of rotation and enclosed by a clamshell oven.

To evaluate the colorimetrics of the pigments in paint, 4 g each of the pigment samples were stirred into 96 g of a mixed-polyester varnish having a solids content of 21% by weight and the mixture was dispersed using a propeller stirrer at 1500 rpm for 15 min. Thereafter the base paint batch was adjusted to a spray viscosity of 18 sec in DIN cup 4 (DIN 53 211) and sprayed onto an unprimed aluminum panel. Following a short flashoff time, a one-component clear varnish based on acrylate/melamine resin (47% by weight solids, adjusted to 23 sec DIN 4) was applied wet on wet. After 30 minutes flashoff at room temperature, the panel was baked at 130° C. for 30 min.

The CIELAB coordinates were subsequently measured with a Multiflash M45 goniospectrophotometer from Optronik (Berlin) at an angle difference of 20°, 45° or 75° to the specular angle. The color coordinates (L, a*, b*, HGD, C*) indicated in the table are based on the standard illuminant D65. L is the lightness, a* is the red or green content and b* is the blue or yellow content. HGD is the hue angle [*] and C* is the chroma.

EXAMPLE 1

75 g of a silvery titania-coated mica pigment (geometric $TiO_2$ layer thickness about 30 nm; IRIODIN® 103 Rutile Sterling Silver; E. Merck, Darmstadt) were inertized in the above-described apparatus by passing 75 l/h of nitrogen over it for one hour. After heating to 850° C. a mixture of 21 l/h of ammonia, 6 l/h of ethane and 10 l/h of nitrogen was passed through the apparatus for 2 h. The subsequent cooling down to room temperature took place under 30 l/h of nitrogen.

The pigment obtained had a deep blue color, a nitrogen content of 1.5% by weight and a carbon content of 0.06% by weight.

Comparative Example C1

Example 1 was repeated using a gas mixture consisting only of 21 l/h of ammonia and 16 l/h of nitrogen.

The pigment obtained was distinctly weaker and more greenish and had a nitrogen content of 0.26% by weight.

Comparative Example C2

Example 1 was repeated using a gas mixture consisting only of 6 l/h of ethane and 31 l/h of nitrogen.

The pigment obtained had a silvery surface color, instead of white, and a carbon content of 4.8% by weight.

TABLE

| Example | Colorimetric data | | | | |
|---|---|---|---|---|---|
| | HGD | C* | L | a* | b* |
| Measuring angle 20° | | | | | |
| 1 | 268.9 | 21.8 | 66.7 | −0.4 | −21.8 |
| C1 | 239.8 | 11.2 | 94.4 | −5.6 | −9.6 |
| C2 | 130.3 | 2.9 | 74.4 | −1.9 | 2.2 |
| Measuring angle 45° | | | | | |
| 1 | 268.4 | 11.4 | 19.3 | −0.3 | −11.4 |
| C1 | 245.4 | 7.8 | 35.9 | −3.2 | −7.0 |
| C2 | 167.4 | 0.8 | 24.9 | −0.8 | 2.2 |
| Measuring angle 75° | | | | | |
| 1 | 267.8 | 8.0 | 7.1 | −0.3 | −0.8 |
| C1 | 254.5 | 7.7 | 18.9 | −2.0 | −7.5 |
| C2 | 303.9 | 1.0 | 12.8 | −0.3 | −1.0 |

We claim:

1. A process for producing bluish luster pigment platelets, comprising:

treating silicatic platelets having a titania coating of a geometric layer thickness of 10 nm to 60 nm with a reducing gas mixture of a vaporized organic compound and ammonia at a temperature of 800°–900° C.

2. The process of claim 1, wherein the organic compound is methane, ethane, propane, n-butane, isobutane or combinations thereof.

3. The process of claim 1, wherein the titania layer thickness ranges from 20–40 nm.

4. The process of claim 1, wherein the silicatic platelets are platelets of mica, talc, or glass flakes.

5. The process of claim 4, wherein the silicatic platelets have an average particle diameter ranging from 1–200 nm.

6. The process of claim 1, wherein said silicatic platelets have a BET surface area ranging from 1–15 m²/g.

7. The process of claim 1, having a volume ratio of ammonia to vaporized organic compound in the range of 99:1 to 50:50.

8. The process of claim 2, wherein said gas mixture has a nitrogen content of 10–60%.

9. Bluish luster pigment platelets, comprising:

silicatic platelets having a titania coating of 10–60 nm, which have been subjected to reduction by treatment with a gas mixture containing ammonia and vaporized organic compound, said bluish luster pigment platelets exhibiting CIELAB color coordinates of $-2 \leq a^* \leq 2$ and $b^* \leq -20$ (measuring angle 20°, standard illuminant D65).

10. The bluish luster pigment platelets of claim 9 wherein the silicatic platelets are mica platelets.

11. A method of coloring paints, inks, plastics, glasses, ceramic products or decorative cosmetic preparations, which comprises:

incorporating the bluish luster pigment platelets of claim 9 into said paints, inks, plastics, glasses, ceramic products or decorative cosmetic preparations.

* * * * *